US009345635B2

(12) United States Patent
Takashima

(10) Patent No.: US 9,345,635 B2
(45) Date of Patent: May 24, 2016

(54) MASSAGER FOR THE BODY CAVITIES AND METHODS FOR USING THE SAME

(71) Applicant: Jiro Takashima, Houston, TX (US)

(72) Inventor: Jiro Takashima, Houston, TX (US)

( * ) Notice: Subject to any disclaimer, the term of this patent is extended or adjusted under 35 U.S.C. 154(b) by 661 days.

(21) Appl. No.: 13/731,839

(22) Filed: Dec. 31, 2012

(65) Prior Publication Data

US 2013/0172793 A1 Jul. 4, 2013

Related U.S. Application Data

(60) Provisional application No. 61/581,991, filed on Dec. 30, 2011.

(51) Int. Cl.

| | |
|---|---|
| ***A61M 11/00*** | (2006.01) |
| ***A61H 15/00*** | (2006.01) |
| ***A61H 21/00*** | (2006.01) |
| ***A63B 23/20*** | (2006.01) |
| *A61H 19/00* | (2006.01) |

(52) U.S. Cl.

CPC ............ *A61H 15/0092* (2013.01); *A61H 21/00* (2013.01); *A63B 23/20* (2013.01); *A61H 19/44* (2013.01); *A61H 2015/0014* (2013.01); *A61H 2201/0157* (2013.01); *A61H 2201/1261* (2013.01); *A61H 2201/1671* (2013.01); *A61H 2201/1695* (2013.01)

(58) Field of Classification Search

CPC ....... A61H 19/00; A61H 19/40; A61H 19/44; A61H 19/50; A61H 21/00; A61H 22/01; A61H 22/0157; A61H 22/1261; A61H 22/1671; A61H 22/22; A61H 22/1695; A61H 20/15; A61H 20/0014; A63B 23/20

USPC ............. 601/121, 134, 135; 600/38; 606/191; D24/215, 211, 214

See application file for complete search history.

(56) References Cited

U.S. PATENT DOCUMENTS

| | | | | | |
|---|---|---|---|---|---|
| 1,612,343 | A | * | 12/1926 | Amussen | 601/135 |
| 2,080,208 | A | * | 5/1937 | Illch | 601/121 |
| 2,477,666 | A | * | 8/1949 | Smallen | 601/135 |
| 2,657,687 | A | * | 11/1953 | Bonham | 601/135 |
| 2,863,445 | A | * | 12/1958 | Johnson | 601/18 |
| D201,598 | S | * | 7/1965 | Gaspar | D24/211 |
| 3,419,268 | A | * | 12/1968 | Bellet | 482/132 |
| 4,014,325 | A | * | 3/1977 | Clarke | 601/121 |
| D254,339 | S | * | 3/1980 | Miller et al. | D1/106 |
| 5,797,950 | A | | 8/1998 | Takashima | |
| 5,861,009 | A | | 1/1999 | Armstrong et al. | |
| D585,627 | S | * | 2/2009 | Wylie | D1/125 |
| D593,277 | S | * | 6/2009 | Wylie | D1/199 |
| 8,182,503 | B2 | | 5/2012 | Takashima | |

* cited by examiner

*Primary Examiner* — Steven Douglas
(74) *Attorney, Agent, or Firm* — Osha Liang LLP

(57) ABSTRACT

A device for massaging a human body cavity includes a substantially cylindrical shaft having a length and a diameter configured to fit inside the human body cavity, wherein an outer surface of the substantially cylindrical shaft forms an asymmetric ridge such that the substantially cylindrical shaft has a non-round cross-sectional profile. A device for massaging a human body cavity may have the asymmetric ridge running in a direction parallel a longitudinal axis of the substantially cylindrical shaft or along a spiral path on an outer surface of the substantially cylindrical shaft. The device for massaging a human body cavity may have a solid core or a hallow core. The device may include a core made of a first material and a surface coating made of a second material.

6 Claims, 3 Drawing Sheets

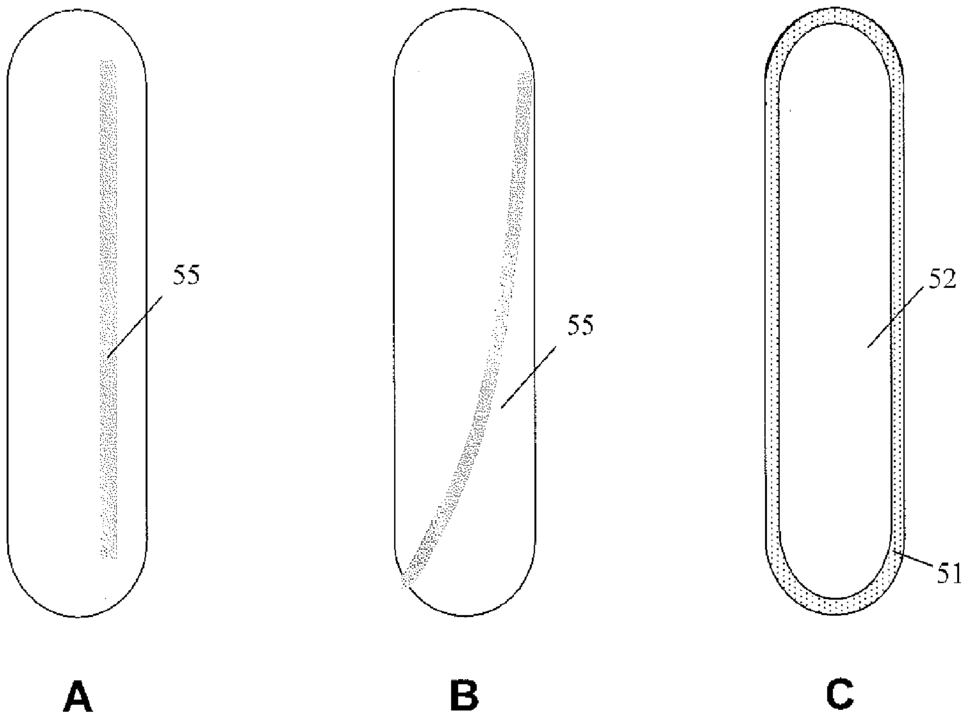
FIG. 5
FIG. 6
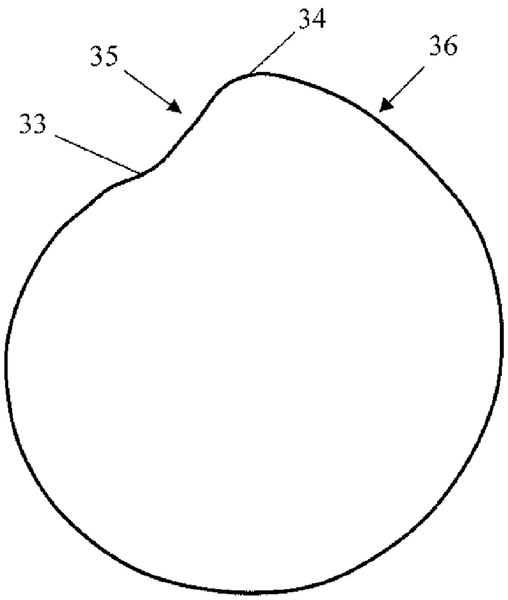

MASSAGER FOR THE BODY CAVITIES AND METHODS FOR USING THE SAME

CROSS REFERENCE TO RELATED APPLICATIONS

This claims the benefits of the Provisional Application No. 61/581,991, filed on Dec. 30, 2011, the disclosure of which is incorporated by reference in its entirety.

FIELD OF THE INVENTION

This invention relates to medical devices that may be used as massagers in body cavities.

BACKGROUND OF THE INVENTION

Non-infectious disorders may be caused by circulation problems and/or homeostasis problems relating to fluid or electrolytes. Such disorders sometimes may be relieved by massage or other physical means. For example, a congested prostate may be remedied with prostate massage. Similarly, it is believed that hemorrhoid massage is effective in relieving the conditions by stimulating blood flow around the areas of the hemorrhoid tissues.

Such prior art medical devices (or massagers) often rely on external forces to effect the massaging actions. U.S. Pat. Nos. 5,797,950, 5,861,000, and 8,182,503 issued to the present inventor, disclose prostate massage devices that can be used without the application of external forces. Instead, these devices harness the contraction and relaxation forces of the sphincter muscles to provide the massage actions. These devices are designed with unique shapes such that the contraction forces of the sphincter are translated into sliding motions of the devices.

These prior art massage devices have proven useful in various applications. There is still a need for devices that can make use of the contraction forces of the muscles to massage human body cavities.

SUMMARY OF THE INVENTION

One aspect of the invention relates to devices for massaging a human body cavity. A device in accordance with one embodiment of the invention includes a substantially cylindrical shaft having a length and a diameter configured to fit inside the human body cavity, wherein an outer surface of the substantially cylindrical shaft forms an asymmetric ridge such that the substantially cylindrical shaft has a non-round cross-sectional profile.

In accordance with some embodiments of the invention, a device for massaging a human body cavity may have the asymmetric ridge running in a direction parallel a longitudinal axis of the substantially cylindrical shaft or along a spiral path on an outer surface of the substantially cylindrical shaft.

In accordance with some embodiments of the invention, a device for massaging a human body cavity may have a solid core or a hallow core. The device may include a core made of a first material and a surface coating made of a second material.

Another aspect of the invention relates to devices for massaging a human body cavity. A device in accordance with one embodiment of the invention includes a substantially cylindrical shaft having a length and a diameter configured to fit inside the human body cavity, wherein the outer surface of said shaft has a curvature that roughly fits within an auxiliary circle, wherein a cross-sectional profile of the outer surface has at least a first portion and a second portion, wherein the first portion has a first point and a second point, and a distance to a center of the auxiliary circle decreases between the first point and the second point of the first portion, wherein the second portion has a first point and a second point, and a distance to the center of the auxiliary circle increases between the first point and the second point of the second portion, and wherein the lengths of the first and second portions of the outer surface can be different or equal.

Other aspects and advantages of the invention will be apparent from the following description and the appended claims.

BRIEF DESCRIPTION OF THE DRAWINGS

FIGS. 5A, 5B, and 5C show examples of alternative designs of massagers in accordance with embodiments of the invention.

FIG. 6 shows a schematic illustrating an asymmetric ridge profile in a cross sectional view of a massager in accordance with one embodiment of the invention.

DETAILED DESCRIPTION

Embodiments of the invention relate to devices for massaging body cavities, such as a human body cavity. Examples of human body cavities, for example, may include colon and urethra. Devices of the invention are designed to move or twist inside a body cavity in response to the compression or pulsation movements of the walls of the body cavities. The movements or twisting actions of a device of the invention inside a body cavity in turn can provide massaging action to the walls of the body cavity.

Devices of the invention may be referred to as massagers. Such devices are dimensioned to fit in the selected body cavities. In general, a device of the invention may have a profile of a substantially cylindrical shaft, which has a length and a diameter configured to fit in the body cavity.

Figure 1:
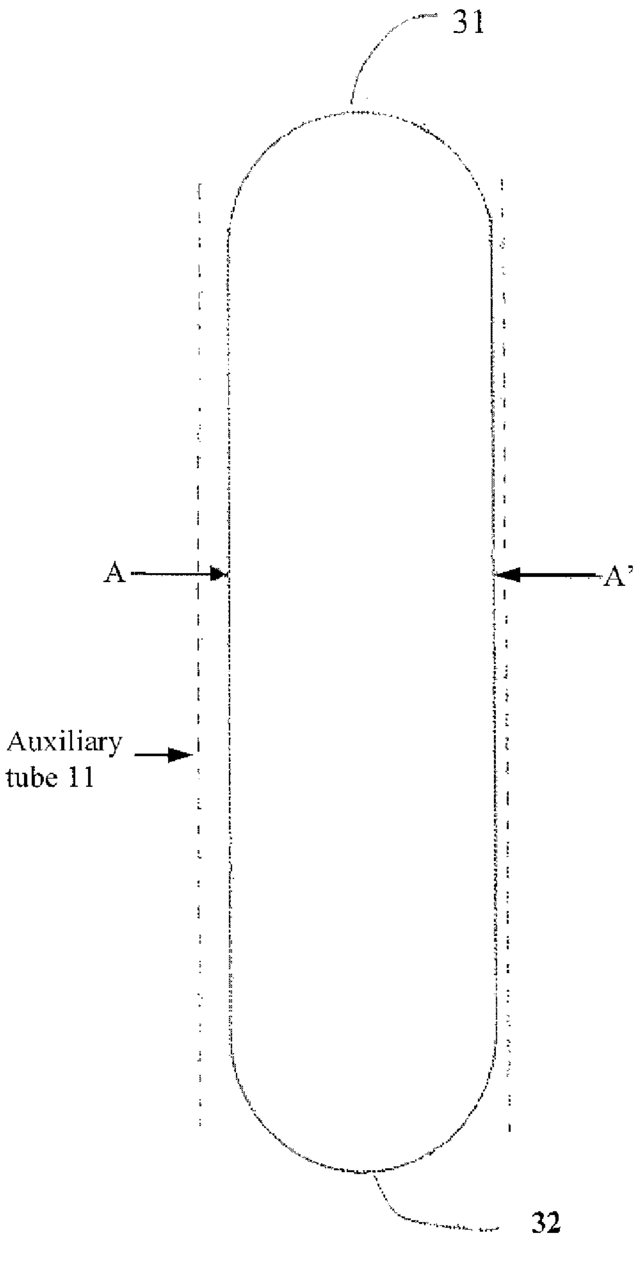
FIG. 1 shows a side view of a body cavity massager 30 in accordance with one embodiment of the present invention.

FIG. 1 shows a side view of a device (a massager) 30 for massaging a body cavity in accordance with one embodiment of the invention. As shown in FIG. 1, the device 30 consists of a generally cylindrical shaft having a first end 31 and a second end 32. The first end 31 and the second end 32 are shown to have a semi-spherical profile in this view. In some embodiments of the invention, the profiles of the first end 31 and/or the second end 32 may have other profiles, such as a conical profile.

While the device 30 shown in FIG. 1 has a general rod shape profile, other embodiments of the invention may have other overall profile, such as a spindle. A device of the invention may also have a mixed profile. Furthermore, the overall profile of the device 30 need not be straight. For example, it may have curvatures (e.g., a curved rod or a sigmoid rod). In addition, the entire device need not have the same shape or profile. For example, one half of the device may have a rod profile as shown in FIG. 1, while the other half may have a spindle profile or a curved profile.

The device 30 may be made of any suitable material, such as metal, plastic, polymer, elastomer, and the like. The substantially cylindrical shaft may have a solid body or a hollow body. In addition, the device 30 may be made of two of more kinds of materials. For example, a device of the invention may have an interior (core) made of one material and the surface made of (or coated with) another material. The surface coating material may be selected to have lower or higher friction such that the device may twist and/or slide in the body cavity in the desire manner.

The diameters and the lengths of the devices may be selected based on the size of the body cavity. In general, the length of device 30 may be between about 1 cm and about 30 cm, preferably between about 3 cm and about 20 cm, and more preferably between about 5 cam and about 10 cm. The diameter of device 30 may be between about 1 mm and about 30 mm, preferably between about 3 mm and about 20 mm, and more preferably between about 5 mm and about 10 mm.

For example, as a hemorrhoid treatment device, the average diameter of a massager may be between about 5 mm and about 25 mm, preferably between about 6 mm and about 12 mm, while the length of a hemorrhoid treatment device may be between about 2 cm and about 15 cm, preferably between about 4 cm and about 10 cm. As another example, the length of a device for massaging a urethra may be between about 2 cm and about 15 cm, preferably between about 4 cm and about 8 cm.

Please note that any numerical range disclosed in this description is intended to include all numbers between the upper and the lower limits, as if all numbers in the range have been explicitly disclosed.

In accordance with embodiments of the invention, the substantially cylindrical shaft has a cross-sectional profile that is not a round circle. In some embodiments of the invention, the shaft may not have non-round cross-section profiles along the entire length of the shaft. Instead, the shaft may have one or more sections having the non-round cross section, while the remaining section may have round cross-sectional profiles. The sections having non-round cross-sectional profiles may account for from about 10% to about 100% of the length of the device.

Figure 2:
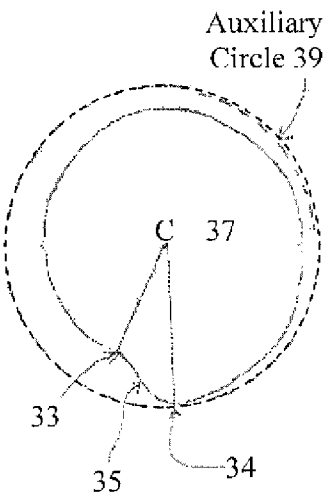
FIG. 2 is a A-A' cross sectional view of the massager 30 of FIG. 1.

FIG. 2 shows an A-A' cross-sectional view of the massager 30 shown in FIG. 1. An auxiliary circle 39 is used to show a relative variation of the curvature of the outer surface of the shaft in the cross-sectional view. C is a center of the auxiliary circle 39. The auxiliary circle 39 is the cross section of the auxiliary tube 11 shown in FIG. 1.

As shown in FIG. 2, tracing the outer surface of the shaft in a counterclockwise direction, the outer surface curvature starts to extend downwardly (inwardly towards the center C, or away from the auxiliary circle 39) from point 34, which is the point on the outer surface farthest from the center C (and closest to the auxiliary circle 39) in this cross sectional view, toward the lowest point 33 (the point closest to the center C and farthest from the auxiliary circle 39) on the outer surface. Then, the outer surface curvature extends upwardly (gradually becoming farther away from the center C and closer to the auxiliary circle) from point 33 and closing at point 34. The downward curvature from point 34 to point 33 is longer than the upward curvature from point 33 to point 34.

The asymmetric curvatures create a "ridge" (or higher points) at point 34 and a "valley" (or lower points) at point 33 on the outer surface of the shaft. FIG. 6 shows a schematic illustrating the "ridge" at point 34 and the "valley" at point 33 in a rotated view (180° rotation), relative to that shown in FIG. 2 or 3. The "ridge" at point 34 has two asymmetric slopes leading away from the "ridge." The steeper and shorter slope 35 leads to the "valley" at point 33, while the shallower and longer slope 36 leads to the other direction. This asymmetric structural feature, which may be referred to as an "asymmetric ridge," will generate asymmetric reaction forces when compressed by muscle contraction in a human body cavity. The asymmetric reaction forces will result in rotation or twisting of the shaft inside a human body cavity.

Figure 3:
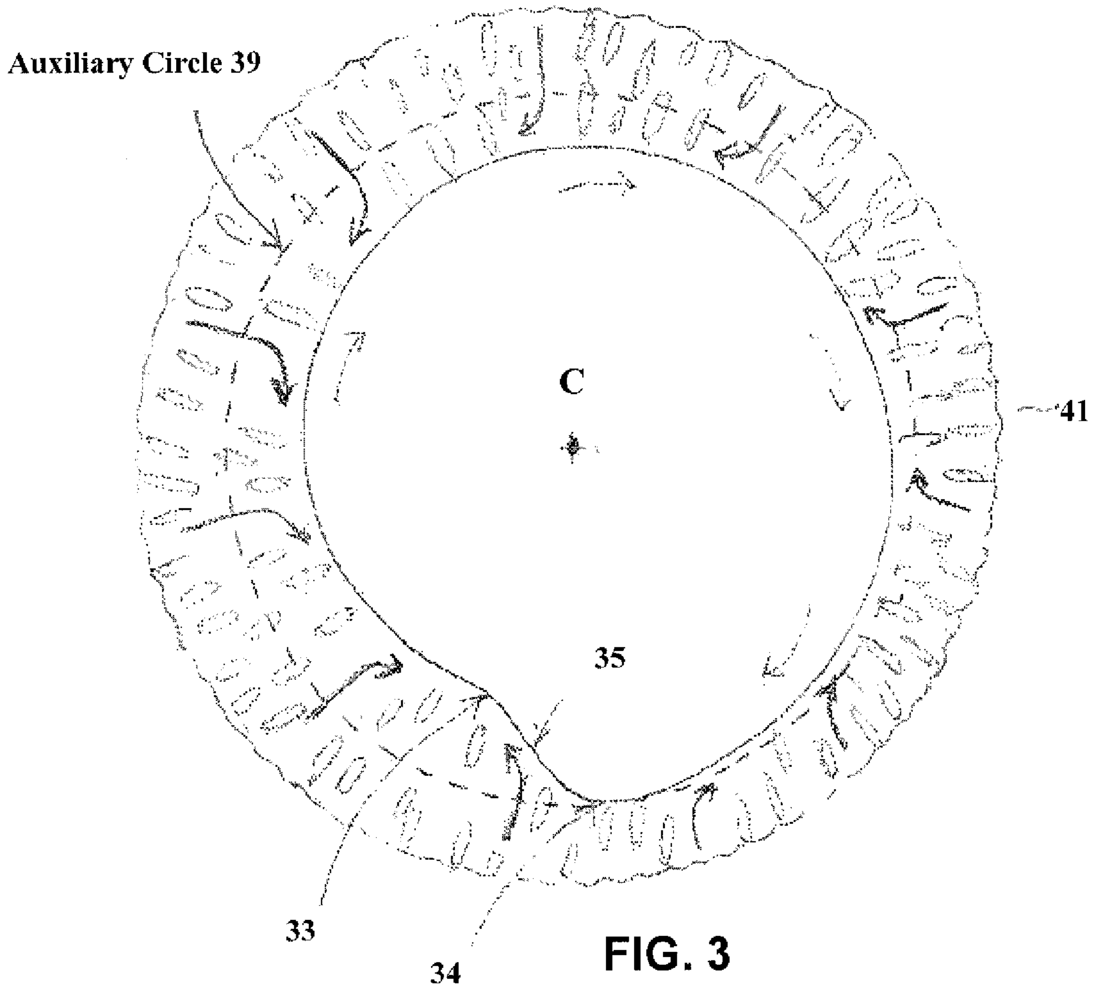
FIG. 3 is a schematic illustrating a possible working mechanism of the massager 30 in accordance with one embodiment of the present invention.

While not intending to be bound by any working mechanism, FIG. 3 shows a schematic illustrating one explanation of how the asymmetric forces acting on the outer surface of the shaft, when the device 30 is compressed by the inner wall muscles in the body cavity 41, may result in twisting actions of the shaft. The vector of the inner cavity pressure goes toward the center of the auxiliary circle, but the contact surface of the inner cavity is not perpendicular to the inner wall of the body cavity 41. Because the length of the down stream surface (i.e., the shallower slope 36 in FIG. 6) from point 34 to the point 33 (in the counterclockwise direction) is longer than the upstream surface (i.e., the steeper slope 35 in FIG. 6) from point 33 to point 34, the total vectors will bend towards the longer downstream curvature, counterclockwise, from highest side 34 to the lowest side 33. The bending of the force vectors and the different lengths of the two slopes will result in a net peripheral force, leading to twisting of the shaft.

Figure 4:
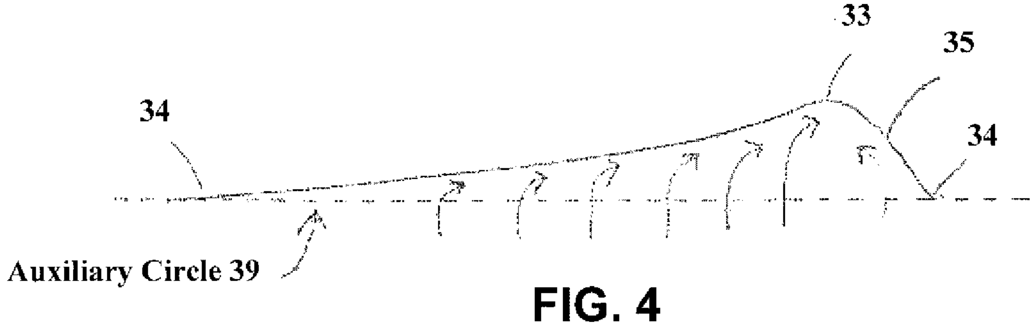
FIG. 4 is a schematic illustrating a possible working mechanism of the massager 30 in accordance with one embodiment of the present invention.

FIG. 4 shows another schematic illustrating an explanation of the working mechanism of the massager 30. Arrows show the directions of vectors that represent the contraction forces acting on the massager 30. In FIG. 4, the dotted line represents the "straightened" auxiliary circle 39, while the solid line from point 34 to point 33 and to point 34 represents the "straightened" outer surface of the shaft. In this schematic view, the vertical distances between the dotted line (auxiliary circle 39) and the solid line 34-33-34 (outer surface of the shaft) represent the distances between the auxiliary circle 39 and the outer surface of the shaft at the corresponding point (cf. FIG. 3).

Referring to FIG. 4, looking from point 34 on the left to point 33 and then to the point 34 on the right, the forces acting on the outer surface of the shaft (illustrated by the arrows) will be twisted toward point 33, illustrated with bending arrows. It is clear that more bending arrows act on the longer (shallower) slope region than on the shorter (steeper) slope region. As a result, the net force is produced that will twist the shaft in the direction shown by the arrows on the longer (shallower) slope region.

FIGS. 3 and 4 illustrate how an asymmetric "ridge" (at point 34) on the outer surface of the shaft can produce twisting actions of a shaft. It is clear that any such asymmetric structural feature along the length of the shaft would produce the effects discussed above. One skilled in the art would appreciate that it is unnecessary to have such asymmetric structural features along the entire length of the shaft.

Furthermore, it is unnecessary that such asymmetric structures be aligned with the longitudinal axis of the shaft. For example, FIG. 5A shows an embodiment that has an "asymmetric ridge" structure 55 aligned with the longitudinal axis of the shaft and spans substantially the entire length of the shaft. On the other hand, FIG. 5B shows another embodiment that has an "asymmetric ridge" structure 55 along a spiral path on the shaft.

As noted above, a massager 30 may have a solid shaft or a hallow shaft. FIG. 5C shows one example of a massager having a hollow core 52 and a shell 51.

As explained with references to FIGS. 3 and 4, devices of the invention will be able to twist inside a human body cavity when compressed by the inner wall of the cavity. Such devices may produce efficient massaging actions in the human body cavities.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A device for massaging a human body cavity, comprising:

a substantially cylindrical shaft having a length and a diameter configured to fit inside the human body cavity, wherein an outer surface of the substantially cylindrical shaft forms an asymmetric ridge such that the substantially cylindrical, shaft has a non-round cross-sectional profile, wherein one side of the asymmetric ridge has a convex curvature and the other side of the asymmetric ridge has a concave curvature in the non-round cross-sectional profile.

2. The device for massaging a human body cavity of claim 1, wherein the asymmetric ridge runs in a direction parallel a longitudinal axis of the substantially cylindrical shaft.

3. The device for massaging a human body cavity of claim 1, wherein the asymmetric ridge runs along a spiral path on an outer surface of the substantially cylindrical shaft.

4. The device for massaging a human body cavity of claim 1, wherein the device has a hollow core.

5. The device for massaging a human body cavity of claim 1, wherein the device comprises a core made of a first material and a surface coating made of a second material.

6. The device for massaging a human body cavity of claim 1, wherein the device is a hemorrhoid massager having a diameter in a range between 5 mm and 25 mm and a length in a range between 4 cm and 10 cm.

* * * * *